(12) United States Patent
Ivie

(10) Patent No.: US 10,765,136 B2
(45) Date of Patent: *Sep. 8, 2020

(54) DIETARY SUPPLEMENT COMPOSITIONS

(71) Applicant: Melaleuca, Inc., Idaho Falls, ID (US)

(72) Inventor: Jeremy Ivie, Ammon, ID (US)

(73) Assignee: Melaleuca, Inc., Idaho Falls, ID (US)

(*) Notice: Subject to any disclaimer, the term of this patent is extended or adjusted under 35 U.S.C. 154(b) by 467 days.

This patent is subject to a terminal disclaimer.

(21) Appl. No.: 14/997,280

(22) Filed: Jan. 15, 2016

(65) Prior Publication Data

US 2016/0360776 A1 Dec. 15, 2016

Related U.S. Application Data

(63) Continuation of application No. 13/885,732, filed as application No. PCT/US2012/038194 on May 16, 2012, now Pat. No. 9,238,045.

(51) Int. Cl.

| | |
|---|---|
| *A61K 36/605* | (2006.01) |
| *A23L 33/105* | (2016.01) |
| *A61K 36/00* | (2006.01) |
| *A23L 33/16* | (2016.01) |
| *A23L 2/39* | (2006.01) |
| *A23L 2/52* | (2006.01) |
| *A61K 33/24* | (2019.01) |
| *A61K 36/258* | (2006.01) |
| *A61K 36/39* | (2006.01) |
| *A61K 36/54* | (2006.01) |
| *A61K 36/82* | (2006.01) |
| *A23L 33/10* | (2016.01) |
| *A23L 33/19* | (2016.01) |
| *A23L 33/115* | (2016.01) |
| *A23L 33/125* | (2016.01) |
| *A23L 33/185* | (2016.01) |
| *A23L 2/56* | (2006.01) |
| *A23L 2/66* | (2006.01) |

(52) U.S. Cl.
CPC ............ *A23L 33/105* (2016.08); *A23L 2/39* (2013.01); *A23L 2/52* (2013.01); *A23L 2/56* (2013.01); *A23L 2/66* (2013.01); *A23L 33/10* (2016.08); *A23L 33/115* (2016.08); *A23L 33/125* (2016.08); *A23L 33/16* (2016.08); *A23L 33/185* (2016.08); *A23L 33/19* (2016.08); *A61K 33/24* (2013.01); *A61K 36/00* (2013.01); *A61K 36/258* (2013.01); *A61K 36/39* (2013.01); *A61K 36/54* (2013.01); *A61K 36/605* (2013.01); *A61K 36/82* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,238,672 B1 | 5/2001 | Chen | |
| 8,420,116 B2 * | 4/2013 | Ivie | .......................... A23L 7/115 |
| | | | 424/439 |
| 9,238,045 B2 * | 1/2016 | Ivie | .......................... A23L 2/39 |
| 2004/0033276 A1 | 2/2004 | Ra et al. | |
| 2006/0172020 A1 | 8/2006 | Djang | |
| 2007/0009615 A1 | 1/2007 | Zhong | |
| 2007/0036874 A1 | 2/2007 | Zhong | |
| 2007/0212460 A1 | 9/2007 | Inoue et al. | |
| 2008/0260934 A1 | 10/2008 | Bok et al. | |
| 2009/0252796 A1 | 10/2009 | Mazed et al. | |
| 2010/0009901 A1 | 1/2010 | Rabovsky et al. | |

FOREIGN PATENT DOCUMENTS

| | | |
|---|---|---|
| JP | 2007/119346 | 5/2007 |
| WO | WO200211562 | 2/2002 |
| WO | WO2007/109802 | 9/2007 |
| WO | WO2009001362 | 12/2008 |

OTHER PUBLICATIONS

Lieberman S. Natural Methods for Accelerating Weight Loss. Alternative and Complementary Therapies 9(6)307-311, Dec. 2003. (Year: 2003).*
Adams., "Chromium prevents diabetes by improving insulin sensitivity," Originally published Nov. 5, 2009, Epub on Mar. 20, 2012, Retrieved Jun. 8, 2017, Retrieved from URL: http://www.naturalnews.com/027398_chromium_diabetes_natural.html#ixzz4Ys6eYETv.
Dudonne et al., "Comparative Study of Antioxidant Properties and Total Phenolic Content of 30 Plant Extracts of Industrial Interest Using DPPH, ABTS, FRAP, SOD, and ORAC Assays," J Agric Food Chem., 57:1768-1774, 2009.
Reay et al., "Effects of Panax ginseng, consumed with and without glucose, on blood glucose levels and cognitive performance during sustained 'mentally demanding' tasks," *J Psychopharmacology.*, 20(6):771-781, 2006.
Reay et al., "Single doses of Panax ginseng (G115) reduce blood glucose levels and improve cognitive performance during sustained mental activity," *J Psychopharmacology.*, 19(4):357-365, 2005.
Su et al., "Total phenolic contents, chelating capacities, and radical-scavenging properties of black peppercorn, nutmeg, rosehip, cinnamon, and oregan leaf," Food Chemistry., 100(3):990-997, 2007.
Abraham et al., "The effects of chromium supplementation on serum glucose and lipids in patients with and without non-insulin-dependent diabetes," *Metabolism*, 41(7):768-771, Jul. 1992.
Althuis et al., "Glucose and insulin responses to dietary chromium supplements: a meta-analysis," *Am J Clin Nutr.*, 76(1):148-155, Jul. 2002.
Andallu and Varadacharyulu, "Antioxidant role of mulberry (*Moms indica* L. cv Anantha) leaves in streptozotocin-diabetic rats," *Clin Chim Acta* 338(1-2):3-10, Dec. 2003.

(Continued)

*Primary Examiner* — Ralph J Gitomer
(74) *Attorney, Agent, or Firm* — Fish & Richardson P.C.

(57) ABSTRACT

This document provides dietary supplement compositions as well as methods for using dietary supplement compositions to control glucose levels. For example, a dietary supplement composition including chromium (e.g., Chromium Oligofructose Complex), a sweet potato extract, and one or more of a mulberry extract, a green tea extract, a cinnamon extract, or a *ginseng* extract (e.g., Korean Red *Ginseng* extract) are provided.

41 Claims, 1 Drawing Sheet

(56) References Cited

OTHER PUBLICATIONS

Andallu and Varadacharyulu, "Gluconeogenic substrates and hepatic gluconeogenic enzymes in streptozotocin-diabetic rats: effect of mulberry (Moms indica L.) leaves," J Med Food., 10(1):41-48, Mar. 2007.

Andallu et al "Effect of mulberry (Moms indica L.) therapy on plasma and erythrocyte membrane lipids in patients with type 2 diabetes," Clin Chim Acta 314(1-2):47-53, Dec. 2001.

Anderson and Polansky, "Tea enhances insulin activity," J Agric Food Chem., 50(24):7182-7186, Nov. 20, 2002.

Anderson et al., "Elevated intakes of supplemental chromium improve glucose and insulin variables in individuals with type 2 diabetes," Diabetes, 46(11):1786-1791, Nov. 1997.

Baker et al., "Effect of cinnamon on glucose control and lipid parameters," Diabetes Care, 31(1):41-43, Jan. 2008.

Bakhtivary, "Herbal medicines in diabetes," Iranian Journal of Diabetes and Obesity, 3(2):88-95, Summer 2011.

Blevins et al., "Effect of cinnamon on glucose and lipid levels in non insulin-dependent type 2 diabetes," Diabetes Care 30(9):2236-2237, Sep. 2007.

Broadhurst et al., "Insulin-like biological activity of culinary and medicinal plant aqueous extracts in vitro," J Agric Food Chem 48(3):849-852, Mar. 2000.

Brown et al., "Chromium deficiency after long-term total parenteral nutrition," Dig Dis Sci., 31(6):661-664, Jun. 1986.

Cao et al., "Cinnamon extract and polyphenols affect the expression of tristetraprolin, insulin receptor, and glucose transporter 4 in mouse 3T3-L1 adipocytes," Arch Biochem Biophys 459(2):214-222, Epub. Jan. 25, 2007.

Cerulli et al., "Chromium picolinate toxicity," Ann Pharmacother., 32(4):428-431, Apr. 1998.

Cheng et al., "Effect of guava (Psidium guajava L.) leaf extract on glucose uptake in rat hepatocytes," J Food Sci., 74(5):H132-H138, Jun. 2009.

Cline et al., "Impaired glucose transport as a cause of decreased insulin-stimulated muscle glycogen synthesis in type 2 diabetes," N Engl J Med., 341(4):240-246, Jul. 22, 1999.

Freund et al., "Chromium deficiency during total parenteral nutrition," JAMA., 241(5):496-498, Feb. 2, 1979.

Fukino et al., "Randomized controlled trial for an effect of green tea consumption on insulin resistance and inflammation markers," J Nutr Sci Vitaminol (Tokyo) 51(5):335-342, Oct. 2005.

Gomes et al., "Anti-hyperglycemic effect of black tea (Camellia sinensis) in rat," J Ethnopharmacol., 45(3):223-226, Mar. 1995.

Hathcock, "Vitamins and minerals: efficacy and safety," Am J Clin Nutr., 66(2):427-437, Aug. 1997.

Higdon and Frei, "Tea catechins and polyphenols: health effects, metabolism, and antioxidant functions," Crit Rev Food Sci Nutr., 43(1):89-143, 2003.

Hosoda et al., "Antihyperglycemic effect of oolong tea in type 2 diabetes," Diabetes Care., 26(6):1714-1718, Jun. 2003.

Imparl-Radosevich et al., "Regulation of PTP-1 and insulin receptor kinase by fractions from cinnamon: implications for cinnamon regulation of insulin signalling," Horm Res., 50(3):177-182, Sep. 1998.

Iso et al., "The relationship between green tea and total caffeine intake and risk for self-reported type 2 diabetes among Japanese adults," Ann Intern Med., 144(8):554-562, Apr. 18, 2006.

Jarvill-Taylor et al., "A hydroxychalcone derived from cinnamon functions as a mimetic for insulin in 3T3-L1 adipocytes," J Am Coll Nutr., 20(4):327-336, Aug. 2001.

Jeejeebhoy et al., "Chromium deficiency, glucose intolerance, and neuropathy reversed by chromium supplementation, in a patient receiving long-term total parenteral nutrition," Am J Clin Nutr., 30(4):531-538, Apr. 1977.

Khan et al., "Cinnamon improves glucose and lipids of people with type 2 diabetes," Diabetes Care, 26(12):3215-3218, Dec. 2003.

Khan et al., "Insulin potentiating factor and chromium content of selected foods and spices," Biol Trace Elem Res., 24(3):183-188, Mar. 1990.

Kim and Kim, "Korean red ginseng stimulates insulin release from isolated rat pancreatic islets," J Ethnopharmacol., 120(2):190-195, Epub. Aug. 15, 2008.

Kim et al., "Anti-diabetic effect of cinnamon extract on blood glucose in db/db mice," J Ethnopharmacol., 104(1-2):119-123, Epub. Oct. 5, 2005.

Kim et al., "Comparison of the effects of Korean ginseng and heat-processed Korean ginseng on diabetic oxidative stress," Am J Chin Med., 36(5):989-1004, 2008.

Kim et al., "Ginsenoside Rg3 Suppresses Palmitate-Induced Apoptosis in MIN6N8 Pancreatic beta-Cells," J Clin Biochem Nutr., 46(1):30-35, Jan. 2010.

Kim et al., "The ginsenoside Rg3 has a stimulatory effect on insulin signaling in L6 myotubes," Biochem Biophys Res Commun., 389(1):70-73, Epub Aug. 21, 2009.

Kimura et al., "Food-grade mulberry powder enriched with 1-deoxynojirimycin suppresses the elevation of postprandial blood glucose in humans," J Agric Food Chem., 55(14):5869-5874, Epub. Jun. 8, 2007.

Lane et al., "Caffeine impairs glucose metabolism in type 2 diabetes," Diabetes Care, 27(8):2047-2048, Aug. 2004.

Lee et al., "Cinnamate supplementation enhances hepatic lipid metabolism and antioxidant defense systems in high cholesterol-fed rats," J Med Food., 6(3):183-191, Fall 2003.

Li et al., "The optimal extraction parameters and anti-diabetic activity of flavonoids from ipomoea batatas leaf," Afr J Tradit Complement Altern Med., 6(2):195-202, Mar. 7, 2009.

Lieberman, "Natural Methods for Accelerating Weight Loss: The Low Glycemic Index Diet, Green Tea, Chromium, and 5-Hydroxytryptophan," Alternative and Complementary Therapies, 9(6):307-311, Dec. 2003.

Liu et al., "Hypoglycemic effects of malonyl-ginsenosides extracted from roots of Panax ginseng on streptozotocin-induced diabetic mice," Phytother Res., 23(10):1426-1430, Oct. 2009.

Lucidi et al., "Effect of chromium supplementation on insulin resistance and ovarian and menstrual cyclicity in women with polycystic ovary syndrome," Fertil Steril., 84(6):1755-1757, Dec. 2005.

Ludvik et al., "Efficacy of Ipomoea batatas (Caiapo) on diabetes control in type 2 diabetic subjects treated with diet," Diabetes Care, 27(2):436-440, Feb. 2004.

Ludvik et al., "Improved metabolic control by Ipomoea batatas (Caiapo) is associated with increased adiponectin and decreased fibrinogen levels in type 2 diabetic subjects," Diabetes Obes Metab., 10(7):586-592, Jul. 2008.

Ludvik et al., "Mode of action of Ipomoea batatas (Caiapo) in type 2 diabetic patients," Metabolism, 52(7):875-880, Jul. 2003.

Mang et al., "Effects of a cinnamon extract on plasma glucose, HbA, and serum lipids in diabetes mellitus type 2," Eur J Clin Invest., 36(5):340-344, May 2006.

Martin et al., "Chromium picolinate supplementation attenuates body weight gain and increases insulin sensitivity in subjects with type 2 diabetes," Diabetes Care., 29(8):1826-1832, Aug. 2006.

Mertz, "Chromium in human nutrition: a review," J Nutr., 123(4):626-633, Apr. 1993.

Mudra et al., "Influence of mulberry leaf extract on the blood glucose and breath hydrogen response to ingestion of 75 g sucrose by type 2 diabetic and control subjects," Diabetes Care, 30(5):1272-1274, Epub. Feb. 15, 2007.

Murata et al., "Antihyperglycemic effects of propolis mixed with mulberry leaf extract on patients with type 2 diabetes," Altern Ther Health Med., 10(3):78-79, May-Jun. 2004.

Nagle et al., "Epigallocatechin-3-gallate (EGCG): chemical and biomedical perspectives," Phytochemistry, 67(17):1849-1855, Sep. 2006.

Park et al., "20(S)-ginsenoside Rg3 enhances glucose-stimulated insulin secretion and activates AMPK," Biol Pharm Bull, 31(4):748-751, Apr. 2008.

(56) References Cited

OTHER PUBLICATIONS

Park et al., "Effects of dietary mulberry, Korean red ginseng, and banaba on glucose homeostasis in relation to PPAR-alpha, PPAR-gamma, and LPL mRNA expressions," *Life Sci.*, 77(26):3344-3354, Nov. 2005

Polychronopoulos et al., "Effects of black and green tea consumption on blood glucose levels in non-obese elderly men and women from Mediterranean Islands (MEDIS epidemiological study)," *Eur J Nutr.*, 47(1):10-16, Epub Jan. 18, 2008.

Qin et al., "Cinnamon extract (traditional herb) potentiates in vivo insulin-regulated glucose utilization via enhancing insulin signaling in rats," *Diabetes Res Clin Pract*, 62(3):139-148, Dec. 2003.

Robinson et al., "Caffeine ingestion before an oral glucose tolerance test impairs blood glucose management in men with type 2 diabetes," *J Nutr.*, 134(10):2528-2533, Oct. 2004.

Ryu et al., "Effects of green tea consumption on inflammation, insulin resistance and pulse wave velocity in type 2 diabetes patients," *Diabetes Res Clin Pract.*, 71(3):356-358, Epub. Sep. 19, 2005.

Sabu et al., "Anti-diabetic activity of green tea polyphenols and their role in reducing oxidative stress in experimental diabetes," *J Ethnopharmacol.*, 83(1-2):109-116, Nov. 2002.

Sakuramata et al., "Effects of combination of Caiapo with other plant-derived substance on anti-diabetic efficacy in KK-Ay mice," *Biofactors.*, 22(1-4):149-152, 2004.

Singer and Geohas, "The effect of chromium picolinate and biotin supplementation on glycemic control in poorly controlled patients with type 2 diabetes mellitus: a placebo-controlled, double-blinded, randomized trial," *Diabetes Technol Ther.*, 8(6):636-643, Dec. 2006.

Vincent, "Mechanisms of chromium action: low-molecular-weight chromium-binding substance," *J Am Coll Nutr.*, 18(1):6-12, Feb. 1999.

Vuksan et al., "Korean red ginseng (Panax ginseng) improves glucose and insulin regulation in well-controlled, type 2 diabetes: results of a randomized, double-blind, placebo-controlled study of efficacy and safety," *Nutr Metab Cardiovasc Dis.*, 18(1):46-56, Epub. Jul. 24, 2006.

Waltner-Law et al., "Epigallocatechin gallate, a constituent of green tea, represses hepatic glucose production," *J Biol Chem.*, 277(38):34933-34940, Sep. 20, 2002.

Wolfram et al., "Epigallocatechin gallate supplementation alleviates diabetes in rodents," *J Nutr.*, 136(10):2512-2518, Oct. 2006.

Wu et al., "Green tea supplementation ameliorates insulin resistance and increases glucose transporter IV content in a fructose-fed rat model," *Eur J Nutr.*, 43(2):116-124, Apr. 2004.

International Search Report and Written Opinion for PCT/US2012/038194, dated Feb. 22, 2013, 12 pages.

International Preliminary Report on Patentability for PCT/US2012/038194, dated Nov. 27, 2014, 8 pages.

Bandara et al., "Bioactivity of cinnamon with special emphasis on diabetes mellitus: a review," International journal of food sciences and nutrition, 63(3):380-6, May 2012.

Canadian Office action in Canadian Application No. 2815999 dated Mar. 21, 2019, 6 pages.

Jeon et al., "Anti-hyperglycemic effect of fermented ginseng in type 2 diabetes mellitus mouse model," Phytotherapy Res., 27(2):166-172, Feb. 2013.

Kumar et al., "Potential antidiabetic and antioxidant activities of Morus indica and Asystasia gangetica in alloxan induced diabetes mellitus," J. Exp. Pharm., 2:29-36, Feb. 2010.

Ooi and Loke "Sweet potato for type 2 diabetes mellitus," Cochrane database syst. rev., (2):CD009128, Feb. 2012.

\* cited by examiner

DIETARY SUPPLEMENT COMPOSITIONS

CROSS-REFERENCE TO RELATED APPLICATIONS

This application is a continuation of U.S. application Ser. No. 13/885,732, filed Nov. 8, 2013 (now U.S. Pat. No. 9,238,045), which is a National Stage Application under 35 U.S.C. § 371 of International Application PCT/US2012/038194, filed May 16, 2012. The disclosures of the prior applications are considered part of (and are incorporated by reference in) the disclosure of this application.

TECHNICAL FIELD

This document relates to dietary supplement compositions. For example, this document relates to methods and materials useful in supplementing the diet of humans or animals to help control blood glucose levels.

BACKGROUND

The blood sugar concentration or blood glucose level is the amount of glucose (sugar) present in the blood of a human or animal. Normally in mammals, the body maintains blood glucose levels at a reference range between about 3.6 and 5.8 mM (mmol/L, i.e., millimoles/liter). When healthy, the body's homeostatic mechanisms keep blood glucose levels within a narrow range. Blood sugar levels can vary over the course of the day and spike after a meal, particularly after a sugar-rich meal. Moreover, certain medical conditions, such as diabetes, can interrupt the body's homeostatic mechanisms that maintain blood glucose levels within a narrow range, thus blood glucose levels may spike even further after a meal for a diabetic. Severe stress, such as trauma, stroke, myocardial infarction, surgery, or illness, can also impact a body's hemostatic mechanisms. High blood sugar levels can have a variety of adverse health effects, including weight gain, kidney damage, neurological damage, cardiovascular damage, and retina damage.

SUMMARY

This document provides dietary supplement compositions that may be consumed with a meal or as a meal supplement to help control blood glucose concentrations. The ingredients of a dietary supplement composition provided herein can work in conjunction with the foods being consumed. In some cases, a dietary supplement composition provided herein can improve the insulin response to a meal and also provide an additional source of glucose. In some cases, a dietary supplement composition provided herein can be a beverage or a powder adapted to be mixed with water to form a beverage.

Dietary supplement compositions provided herein can include a chromium, a sweet potato extract, and one or more of a mulberry extract, a green tea extract, a cinnamon extract, or a *ginseng* extract. A dietary supplement composition provided herein can increase the ability of insulin-sensitized cells to uptake glucose, reduce fasting blood glucose levels, lower the glycemic index of foods consumed therewith, reduce insulin resistance, improve glucose tolerance, up-regulate Glucokinase MRNA expression, activate insulin receptors, increase glycogen synthase activity, and/or stimulate the release of insulin. In some cases, a dietary supplement composition provided herein can aid in insulin uptake/release, and support normal metabolism of blood sugar.

A dietary supplement composition can include a sweet potato extract, a chromium, and one or more ingredients selected from mulberry extract, a green tea extract, a cinnamon extract, and a *ginseng* extract. In some cases, a dietary supplement composition provided herein includes a sweet potato extract, a chromium, a mulberry extract, a green tea extract, a cinnamon extract, and a *ginseng* extract.

A dietary supplement composition provided herein can be in the form of a dry powder. For example the dry powder can be in the form a shake mix or included in a capsule. For example, a dry powder dietary supplement composition provided herein can be mixed with a liquid (e.g., water) to form a solution or aqueous slurry that can be consumed by a user as a beverage. In some cases, a dry powder dietary supplement composition provided herein can be packaged as a bulk product with or without a measuring spoon, as a single serving package containing an amount of a dry powder dietary supplement composition to be mixed with a liquid (e.g., 4 ounces water, 6 ounces water, 8 ounces water, 12 ounces water). In some cases, a dry powder dietary supplement composition provided herein includes between 0.1 weight percent and 2.0 weight percent of one or more sweet potato extracts. In some cases, a dry powder dietary supplement composition provided herein includes between 0.01 weight percent and 0.1 weight percent of a chromium containing compound. In some cases, a dry powder dietary supplement composition provided herein includes between 0.0001 and 0.001 weight percent elemental chromium. In some cases, a dry powder dietary supplement composition provided herein includes between 0.5 weight percent and 10 weight percent one or more mulberry extracts. In some cases, a dry powder dietary supplement composition provided herein includes between 0.1 weight percent and 5 weight percent one or more *ginseng* extracts. In some cases, a dry powder dietary supplement composition provided herein includes between 0.1 weight percent and 2 weight percent one or more cinnamon extracts. In some cases, a dry powder dietary supplement composition provided herein includes between 0.1 weight percent and 1.0 weight percent one or more green tea extracts. In some cases, a dry powder dietary supplement composition provided herein includes between 5 weight percent and 85 weight percent protein. In some cases, a dry powder dietary supplement composition provided herein includes between 5 weight percent and 35 weight percent soluble fiber.

A dietary supplement composition provided herein can be in the form of a beverage. A beverage dietary supplement composition provided herein can include a solution and/or a slurry. In some cases, a beverage dietary supplement composition provided herein can include at least 10 mg of a sweet potato extract per 8 fluid ounce serving of the beverage. In some cases, a beverage dietary supplement composition provided herein can include 1000 mg or less of a sweet potato extract per 8 fluid ounce serving of the beverage. In some cases, a beverage dietary supplement composition provided herein can include at least 10 µg of elemental chromium per 8 fluid ounce serving of the beverage. In some cases, a beverage dietary supplement composition provided herein can include 360 µg or less of elemental chromium per 8 fluid ounce serving of the beverage. In some cases, a beverage dietary supplement composition provided herein can include at least 50 mg of a mulberry extract per 8 fluid ounce serving of the beverage. In some cases, a beverage dietary supplement composition provided herein can include 5000 mg or less of a mulberry extract per 8 fluid ounce serving of the beverage. In some cases, a beverage dietary supplement composition provided herein can include at least 10 mg of a green tea extract per 8 fluid ounce serving of the beverage. In some cases, a beverage dietary supplement composition provided herein can include 1000 mg or less of a green tea extract per 8 fluid ounce serving of the beverage. In some cases, a beverage dietary supplement composition provided herein can include at least 10 mg of a cinnamon extract per 8 fluid ounce serving of the beverage. In some cases, a beverage dietary supplement composition provided herein can include 1000 mg or less of a cinnamon extract per 8 fluid ounce serving of the beverage. In some cases, a beverage dietary supplement composition provided herein can include at least 10 mg of a *ginseng* extract per 8 fluid ounce serving of the beverage. In some cases, a beverage dietary supplement composition provided herein can include 2000 mg or less of a *ginseng* extract per 8 fluid ounce serving of the beverage. For example, a beverage dietary supplement composition provided herein can include 1 to 20 mg of chromium oligofructose complex per 8 fluid ounce serving of the beverage, 400 to 800 mg mulberry extract per 8 fluid ounce serving of the beverage, 100 to 300 mg sweet potato extract per 8 fluid ounce serving of the beverage, 50 to 200 mg green tea extract per 8 fluid ounce serving of the beverage, 100 to 300 mg cinnamon extract per 8 fluid ounce serving of the beverage, and 100 to 400 mg *ginseng* extract per 8 fluid ounce serving of the beverage.

A dietary supplement composition provided herein can be in the form of a tablet, bar, soup, soup mix, or other suitable ingestible carrier as is known in the art, For example, a bar, a can of soup, or a packaged soup mix can include a dietary supplement composition provided herein. In some cases, a bar, a can of soup, or a packaged soup mix provided herein can include at least 10 mg of a sweet potato extract. In some cases, a bar, a can of soup, or a packaged soup mix provided herein can include 1000 mg or less of a sweet potato extract. In some cases, a bar, a can of soup, or a packaged soup mix provided herein provided herein can include at least 10 μg of elemental chromium. In some cases, a bar, a can of soup, or a packaged soup mix provided herein can include 360 μg or less of elemental chromium. In some cases, a bar, a can of soup, or a packaged soup mix provided herein can include at least 50 mg of a mulberry extract. In some cases, a bar, a can of soup, or a packaged soup mix provided herein can include 5000 mg or less of a mulberry extract. In some cases a bar, a can of soup, or a packaged soup mix provided herein can include at least 10 mg of a green tea extract. In some cases, a bar, a can of soup, or a packaged soup mix provided herein can include 1000 mg or less of a green tea extract. In some cases, a bar, a can of soup, or a packaged soup mix provided herein can include at least 10 mg of a cinnamon extract. In some cases, a bar, a can of soup, or a packaged soup mix provided herein can include 1000 mg or less of a cinnamon extract. In some cases, a bar, a can of soup, or a packaged soup mix provided herein can include at least 10 mg of a *ginseng* extract. In some cases, a bar, a can of soup, or a packaged soup mix provided herein can include 2000 mg or less of a *ginseng* extract. For example, a bar, a can of soup, or a packaged soup mix provided herein can include 50 to 180 μg chromium oligofructose complex, 400 to 800 mg mulberry extract, 100 to 300 mg sweet potato extract, 50 to 200 mg green tea extract, 100 to 300 mg cinnamon extract, and 100 to 400 mg *ginseng* extract.

A dietary supplement composition provided herein can include additional ingredients such as fillers, thickeners, proteins, creamers, sweeteners, flavorants, or a combination thereof. In some case, a dietary supplement composition can include between 5 to 25 grams of protein per serving. In some case, a dietary supplement composition can include less than 10 grams of total fat per serving. In some case, a dietary supplement composition can include less than 5 grams of sugars per serving. In some case, a dietary supplement composition can include less than 10 grams of soluble fiber per serving. In some cases, a serving can be 8 ounces of a beverage dietary supplement composition or an amount of dry powder dietary supplement composition intended to be mixed with a liquid to form a single serving. For example, 8 ounces of water could be combined with about 30 grams of a dry powder dietary supplement composition provided herein to form a beverage dietary supplement composition. In some cases, a container or package containing a dry powder dietary supplement composition provided herein can include a measuring scoop or spoon sized to measure out a single serving of a dry powder dietary supplement composition provided herein.

A dietary supplement composition provided herein can include one or more biologically active form of chromium. In some cases, a dietary supplement composition provided herein can include chromium oligofructose complex. In some cases, a dietary supplement composition provided herein can include chromium yeast. In some cases, a dietary supplement composition provided herein can include a chromium picolinate. In some cases, a dietary supplement composition provided herein can include a chromium chelate.

A dietary supplement composition provided herein can include phenols. In some cases, a green tea extract included in a dietary supplement composition provided herein includes less than 85% phenols. In some cases, a cinnamon extract included in a dietary supplement composition provided herein includes between 20% and 40% phenols.

A dietary supplement composition provided herein can include ginsenosides. In some cases, a *ginseng* extract included in a dietary supplement composition provided herein includes less than 20% ginsenosides. For example, a *ginseng* extract of a dietary supplement composition provided herein can include between 5% and 10% ginsenosides. In some cases, a dietary supplement composition provided herein can include Korean Red *ginseng* extract.

A dietary supplement composition provided herein can include an artificial sweetener. For example, a dietary supplement composition provided herein can include a high intensity sweetener, such as saccharine, sucralose, aspartame, acesulfame potassium, or combinations thereof. In some cases, a dietary supplement composition provided herein can be substantially free of hydrogenated or trans fats. In some cases, a dietary supplement composition provided herein can be substantially free of corn syrup. In some cases, a dietary supplement composition provided herein can be substantially free of artificial colors, artificial flavors, and chemical preservatives. In some cases, a dietary supplement composition provided herein can be substantially free of vitamins or mineral fortification other than chromium.

A method for controlling blood glucose concentrations can include consuming a dietary supplement composition provided herein. In some cases, a method for controlling blood glucose concentrations provided herein can include consuming a dietary supplement composition provided herein with a meal. In some cases, a method for controlling blood glucose concentrations provided herein can include consuming a dietary supplement composition provided herein between meals.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description and drawings, and from the claims.

DETAILED DESCRIPTION

Figure 2:
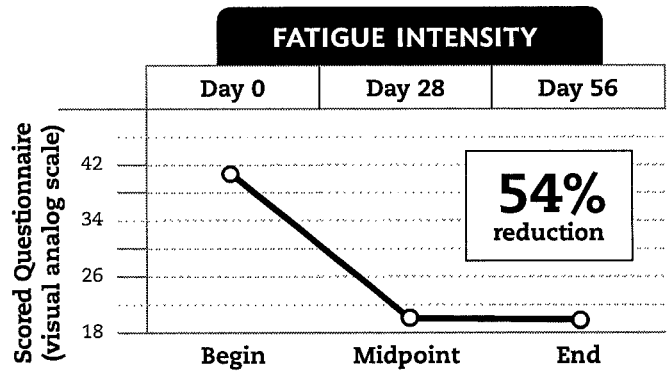
FIG. 2 is a chart of fatigue intensity levels of test participants using a dietary supplement composition provided herein.

This document provides dietary supplement compositions that may be consumed with a meal or as a meal supplement to help control blood glucose concentrations. A dietary supplement composition provided herein can be taken with a meal or between meals. A dietary supplement compositions provided herein can be configured to include chromium, a sweet potato extract, and one or more of a mulberry extract, a green tea extract, a cinnamon extract, or a *ginseng* extract.

The ingredients of a dietary supplement composition provided herein can work in conjunction with the foods being consumed. In some cases, a dietary supplement composition provided herein can improve the insulin response to a meal and can provide an additional source of glucose. A dietary supplement composition provided herein can be consumed between meals as a meal supplement.

In some cases, a dietary supplement composition provided herein can be a beverage. In some cases, a dietary supplement composition provided herein can be provided in a powdered form that can be combined with a liquid to form a beverage. For example, a package can include between 10 grams and 100 grams of a dry powered form of a dietary supplement composition provided herein and can be designed to be mixed with water (or another consumable liquid) to form a beverage. A beverage including a dietary supplement composition provided herein can be an aqueous solution or slurry. In some case, a dietary supplement composition can be provided as an encapsulated product.

A dietary supplement composition provided herein can be in the form of a liquid, solution, suspension, pill, capsule, tablet, gel cap, powder, or gel. For oral administration, tablets or capsules can be prepared by conventional means with acceptable excipients such as binding agents, fillers, lubricants, disintegrants, or wetting agents. The tablets can be coated, if desired. Liquid preparations for oral administration can take the form of, for example, solutions, syrups, or suspension, or they can be presented as a dry product for constitution with saline or other suitable liquid vehicle before use. Dietary supplement compositions of the type described herein also can contain acceptable additives as will be understood by one skilled in the art depending on the particular form of the dietary composition. Non-limiting examples of such additives include suspending agents, emulsifying agents, non-aqueous vehicles, preservatives, buffer salts, flavoring, coloring, and sweetening agents as appropriate. Non-limiting examples of specific additives include: gelatin, glycerin, water, beeswax, lecithin, cocoa, caramel, titanium dioxide, or carmine. Preparations for oral administration also can be suitably formulated to give controlled release of the ingredients.

In some cases, a dietary supplement composition provided herein can contain an acceptable carrier for administration to a mammal (e.g., a human), including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration.

In some cases, the dietary composition can be included as a supplement in a carrier food form, for example in the form of a shake, bar, or soup. For example, a blend of ingredients provided herein can be incorporated into a base of soy crisps, syrups, sweeteners, and fiber sources to produce an extruded protein bar. In some cases, the product can be in the form of a chocolate bar (e.g., a chocolate protein bar). The chocolate bar can be dark chocolate, light chocolate, white chocolate, any other type of chocolate, or a mixture thereof. Optionally, caramel, peanut butter, or any of a variety of other flavorings or food products can be added to the bar. A bar can be, for example, about 50 grams in weight, and can provide one serving of pre-blend. A bar can be of greater or lesser weight (e.g., 25 or 100 grams), and can provide more or less and one serving of pre-blend (e.g. half a serving or two servings). The product can be coated or partially coated in chocolate (or other flavor), and each bar can be individually packaged. The product can be coated or partially coated in dark chocolate, light chocolate, any other type of chocolate, or a mixture thereof. The final product can be consumed as one serving as either a meal replacement or snack item.

In another example, a blend of ingredients provided herein can be added to a meal replacement shake base. The configuration of a suitable shake base is known in the art and will be apparent to one skilled in the art in view of the disclosure herein. The final shake can be any flavor (e.g., chocolate, vanilla, or strawberry). Final serving size can be, for example, 30 g to be dispersed into 8 ounces of milk or water (or other suitable liquid) to form one complete serving. Final serving size can be greater or lesser than 30 grams (e.g., 15 or 60 grams) and can provide more or less than one complete serving (e.g., half a serving or two servings).

A dietary supplement composition provided herein can include one or more biologically active form of chromium (Cr). A biologically active form of chromium (Cr) can participate in glucose metabolism by enhancing the effects of insulin. For example, a dietary supplement composition provided herein can include a biologically active form of chromium such that the composition can increase the ability of an insulin-sensitized cell to uptake glucose. The biologically active form of chromium can be a low-molecular-weight chromium-binding substance (LMWCr). For example, a biologically active form of chromium can be a naturally-occurring oligo-peptide. In some cases, a dietary supplement composition provided herein can include chromium oligofructose complex. Chromium oligofructose complex can also be called chromium amino acid polyfructose complex. For example, chromium amino acid polyfructose complex is described in U.S. Patent Application Publication No. 2010/0009901 (see e.g., paragraph 210), which is hereby incorporated by referenced. In some cases, a dietary supplement composition provided herein can include chromium yeast. In some cases, a dietary supplement composition provided herein can include a chromium picolinate. In some cases, a dietary supplement composition provided herein can include a chromium chelate.

Any appropriate amount of chromium can be included within a dietary supplement composition provided herein. For example, a dietary supplement composition provided herein can include up to 360 µg of elemental chromium per serving (e.g., up to 300 µg/serving, up to 250 µg/serving, up to 200 µg/serving, up to 180 µg/serving, up to 150 µg/serving, or up to 120 µg/serving). In some cases, a dietary supplement composition provided herein can include at least 10 µg of elemental chromium per serving (e.g., at least 20 µg/serving, at least 50 µg/serving, at least 80 µg/serving or at least 100 µg/serving). In some cases, a dietary supplement composition provided herein can include between 20 µg and 360 µg of elemental chromium per serving, between 50 µg and 180 µg of elemental chromium per serving, between 80 µg and 150 µg of elemental chromium per serving, or between 100 µg and 120 µg of elemental chromium per serving. In some cases, a dietary supplement composition provided herein can be in the form of a beverage and the amounts per serving of elemental chromium described herein can be per 8 fluid ounce serving of that beverage. In some cases, a dietary supplement composition provided herein can be in a powdered form adapted to be mixed with a liquid to form a beverage and the amounts per serving of chromium described herein can be per 30 grams of the powdered dietary supplement composition. In some cases, a dietary supplement composition provided herein can be part of an encapsulated dietary supplement having the amounts per serving of chromium described herein.

In some cases, a dietary supplement composition provided herein can be in a powdered form and include between 0.01 weight percent and 0.1 weight percent of a chromium containing compound (e.g., Chromium Oligofructose Complex) (e.g., between 0.02 weight percent and 0.08 weight percent, between 0.03 weigh percent and 0.06 weight percent, or between 0.04 weight percent and 0.05 weight percent). In some cases, a chromium containing compound in a dietary supplement composition provided herein can include between 0.1 and 50 weight percent elemental chromium (e.g., between 0.5 weight percent and 10 weight percent, or between 1 weigh percent and 5 weight percent).

When a dietary supplement composition provided herein is consumed, chromium can be stored within the consumer's body over the course of one or more days. Chromium can be maintained at a consistent ratio within the body. Chromium can be incorporated in protein structures (e.g., enzymes and hormones) for use within the body.

A dietary supplement composition provided herein can include one or more green tea extracts. Green and black tea both originate from the leaves of the *Camellia sinensis* plant. Green tea is heated to inactivate the enzymes that would otherwise oxidize the freshly collected leaves. A dietary supplement composition provided herein can be configured to include a green tea extract in an amount effective to improve insulin response by making cells more tolerant and/or to increase cellular production of glucokinase, which can break down glucose for use as energy.

In some cases, a dietary supplement composition provided herein can include a green tea extract that includes phenols. For example, a green tea extract incorporated into a dietary supplement composition provided herein can include at least 70% phenols (e.g., at least 80% phenols, at least 85% phenols, or between 85% and 95% phenols).

Any appropriate amount of green tea extract(s) can be included within a dietary supplement composition provided herein. For example, a dietary supplement composition provided herein can include up to 1000 mg of green tea extract per serving (e.g., up to 800 mg/serving, up to 600 mg/serving, up to 400 mg/serving, up to 300 mg/serving, up to 200 mg/serving, or up to 150 mg/serving). In some cases, a dietary supplement composition provided herein can include at least 10 mg of green tea extract per serving (e.g., at least 25 mg/serving, at least 50 mg/serving, at least 75 mg/serving, or at least 100 mg/serving). In some cases, a dietary supplement composition provided herein can include between 10 and 1000 mg of green tea extract per serving, between 25 and 400 mg of green tea extract per serving, between 50 and 200 mg of green tea extract per serving, or between 100 and 150 mg of green tea extract per serving.

In some cases, a dietary supplement composition provided herein can be in the form of a beverage and the amounts per serving of green tea extract(s) described herein can be per 8 fluid ounce serving of that beverage. In some cases, a dietary supplement composition provided herein can be in a powdered form adapted to be mixed with a liquid to form a beverage and the amounts per serving of green tea extract(s) described herein can be per 30 grams of the powdered dietary supplement composition. In some cases, a dietary supplement composition provided herein can be part of an encapsulated dietary supplement having the amounts per serving of green tea extract(s) described herein.

In some cases, a dietary supplement composition provided herein can be in a powdered form and include between 0.1 weight percent and 1.0 weight percent green tea extract(s) (e.g., between 0.2 weight percent and 0.8 weight percent, between 0.3 weigh percent and 0.6 weight percent, or between 0.4 weight percent and 0.5 weight percent).

A dietary supplement composition provided herein can include one or more cinnamon extracts. A dietary supplement composition provided herein can be configured to include a cinnamon extract in an amount effective to increase a body's ability to make glycogen. *Cinnamomum verum* is a small evergreen tree, the bark of which is a common culinary spice. Most cinnamon sold in the United States and Canada is actually derived from *C. aromaticum* or *C. cassia*, sometimes called "Chinese cinnamon" to distinguish it from *C. verum*. In some cases, a dietary supplement composition provided herein can include an extract from *Cinnamomum verum, Cinnamomum aromaticum*, and/or *Cinnamomum cassia*.

In some cases, a dietary supplement composition provided herein can include a cinnamon extract that includes phenols. For example, a cinnamon extract incorporated into a dietary supplement composition provided herein can include between 10% and 50% phenols (e.g., between 20% and 40% phenols, between 25% and 35% phenols, between 28% and 32% phenols, or about 30% phenols).

Any appropriate amount of cinnamon extract(s) can be included within a dietary supplement composition provided herein. For example, a dietary supplement composition provided herein can include up to 1000 mg of cinnamon extract per serving (e.g., up to 800 mg/serving, up to 600 mg/serving, up to 400 mg/serving, up to 300 mg/serving, up to 250 mg/serving, or up to 225 mg/serving). In some cases, a dietary supplement composition provided herein can include at least 10 mg of cinnamon extract per serving (e.g., at least 50 mg/serving, at least 100 mg/serving, at least 150 mg/serving, or at least 175 mg/serving). In some cases, a dietary supplement composition provided herein can include between 10 and 1000 mg of cinnamon extract per serving, between 50 and 600 mg of cinnamon extract per serving, between 100 and 300 mg of cinnamon extract per serving, or between 175 and 225 mg of cinnamon extract per serving.

In some cases, a dietary supplement composition provided herein can be in the form of a beverage and the amounts per serving of cinnamon extract(s) described herein can be per 8 fluid ounce serving of that beverage. In some cases, a dietary supplement composition provided herein can be in a powdered form adapted to be mixed with a liquid to form a beverage and the amounts per serving of cinnamon extract(s) described herein can be per 30 grams of the powdered dietary supplement composition. In some cases, a dietary supplement composition provided herein can be part of an encapsulated dietary supplement having the amounts per serving of cinnamon extract(s) described herein.

In some cases, a dietary supplement composition provided herein can be in a powdered form and include between 0.1 weight percent and 2.0 weight percent cinnamon extract(s) (e.g., between 0.2 weight percent and 1.5 weight percent, between 0.3 weigh percent and 1.0 weight percent, between 0.4 weigh percent and 0.8 weight percent, or between 0.5 weight percent and 0.7 weight percent).

A dietary supplement composition provided herein can include one or more mulberry extracts. In some cases, a dietary supplement composition provided herein can include an extract from the Mulberry leaf (e.g., *Morus alba* L. or *Morus alba*). In some cases, a dietary supplement composition provided herein can include a mulberry extract that includes 1-deoxynojirimycin (DNJ).

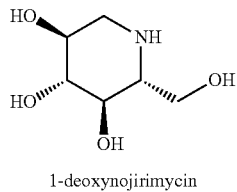

1-deoxynojirimycin

A dietary supplement composition provided herein can be configured to include a mulberry extract in an amount effective to lower the glycemic index of foods consumed with a dietary supplement composition provided herein. Lowering the glycemic index of foods can reduce the release of insulin, which can result in a more even control of blood glucose levels.

Any appropriate amount of mulberry extract(s) can be included within a dietary supplement composition provided herein. For example, a dietary supplement composition provided herein can include up to up to 5000 mg of mulberry extract per serving (e.g., up to 4000 mg/serving, up to 3000 mg/serving, up to 2000 mg/serving, up to 1000 mg/serving, up to 800 mg/serving, or up to 650 mg/serving). In some cases, a dietary supplement composition provided herein can include at least 50 mg of mulberry per serving (e.g., at least 100 mg/serving, at least 200 mg/serving, at least 400 mg/serving, or at least 550 mg/serving). In some cases, a dietary supplement composition provided herein can include between 50 and 5000 mg of mulberry extract per serving, between 200 and 1000 mg of mulberry extract per serving, between 400 and 800 mg of mulberry extract per serving, or between 550 and 650 mg of mulberry extract per serving.

In some cases, a dietary supplement composition provided herein can be in the form of a beverage and the amounts per serving of mulberry extract(s) described herein can be per 8 fluid ounce serving of that beverage. In some cases, a dietary supplement composition provided herein can be in a powdered form adapted to be mixed with a liquid to form a beverage and the amounts per serving of mulberry extract(s) described herein can be per 30 grams of the powdered dietary supplement composition. In some cases, a dietary supplement composition provided herein can be part of an encapsulated dietary supplement having the amounts per serving of mulberry extract(s) described herein.

In some cases, a dietary supplement composition provided herein can be in a powdered form and include between 0.5 weight percent and 10 weight percent mulberry extract(s) (e.g., between 1.0 weight percent and 5.0 weight percent, between 1.5 weigh percent and 3.0 weight percent, between 1.8 weigh percent and 2.3 weight percent, or between 2.0 weight percent and 2.1 weight percent).

A dietary supplement composition provided herein can include one or more sweet potato extracts. A dietary supplement composition provided herein can be configured to include a sweet potato extract in an amount effective to stabilize blood sugar levels, lower insulin resistance, and/or improve metabolic control in type 2 diabetic patients. In some cases, a dietary supplement composition provided herein can include a sweet potato extract that includes phytic acid. In some cases, a dietary supplement composition provided herein can include a sweet potato extract that includes fiber, complex carbohydrates, protein, vitamins A and C, iron, and/or calcium. In some cases, a dietary supplement composition provided herein can include a sweet potato extract that includes a peptic substance. In some cases, a dietary supplement composition provided herein can include a sweet potato extract that includes uronic acid and/or methoxyl. In some cases, a dietary supplement composition provided herein can include a sweet potato extract that includes phytin, monoaminophosphatides (e.g., probably lecithin and cephalin), organic acids (e.g., oxalic acid), phytosterolin, phytosterol, resins, tannins, and coloring matter. In some cases, the sweet potato extract in the dietary supplement compositions provided herein can be an extract of Caiapo. In some cases, the sweet potato extract in the dietary supplement compositions provided herein can be an extract of *ipomoea batatas* (a white-skinned sweet potato). In some cases, sweet potato extract can enhance the effect of chromium.

Any appropriate amount of sweet potato extract(s) can be included within a dietary supplement composition provided herein. For example, a dietary supplement composition provided herein can include up to up to 1000 mg of sweet potato extract per serving (e.g., up to 800 mg/serving, up to 600 mg/serving, up to 400 mg/serving, up to 300 mg/serving, up to 250 mg/serving, or up to 225 mg/serving). In some cases, a dietary supplement composition provided herein can include at least 10 mg of sweet potato extract per serving (e.g., at least 50 mg/serving, at least 100 mg/serving, at least 150 mg/serving, or at least 175 mg/serving). In some cases, a dietary supplement composition provided herein can include between 10 and 1000 mg of sweet potato extract per serving, between 50 and 600 mg of sweet potato extract per serving, between 100 and 300 mg of sweet potato extract per serving, or between 175 and 225 mg of sweet potato extract per serving.

In some cases, a dietary supplement composition provided herein can be in the form of a beverage and the amounts per serving of sweet potato extract(s) described herein can be per 8 fluid ounce serving of that beverage. In some cases, a dietary supplement composition provided herein can be in a powdered form adapted to be mixed with a liquid to form a beverage and the amounts per serving of sweet potato extract(s) described herein can be per 30 grams of the powdered dietary supplement composition. In some cases, a dietary supplement composition provided herein can be part of an encapsulated dietary supplement having the amounts per serving of sweet potato extract(s) described herein.

In some cases, a dietary supplement composition provided herein can be in a powdered form and include between 0.1 weight percent and 2.0 weight percent sweet potato extract(s) (e.g., between 0.2 weight percent and 1.5 weight percent, between 0.3 weigh percent and 1.0 weight percent, between 0.4 weigh percent and 0.8 weight percent, or between 0.5 weight percent and 0.7 weight percent).

A dietary supplement composition provided herein can include one or more *ginseng* extracts. In some cases, a dietary supplement composition provided herein can include red *ginseng* extract (e.g., Korean Red *Ginseng* extract). In some cases, a dietary supplement composition provided herein can include *Panax ginseng* extract. A dietary supplement composition provided herein can be configured to include a *ginseng* extract in an amount effective to increase the release of insulin with consumption of glucose, to protect beta cells, and/or improve glucose and insulin regulation. In some cases, a dietary supplement composition provided herein includes *ginseng* extract combined with chromium and mulberry extract and can function to provide efficient energy deployment within a consumer's body.

Red *ginseng* refers to the way the *ginseng* is prepared. For example, red *ginseng* can be prepared by steam-curing aged and un-peeled *ginseng* roots. In some cases, *ginseng* roots can be aged for about 6 years prior to steam-curing. In some cases, *ginseng* can be steam-curing using standard boiling temperatures of about 100° C. In some case, the steam-cured *ginseng* can be dried. Steam-curing can give the *ginseng* a glossy reddish-brown color when dried. In some cases, steaming the root can prevent the breakdown of active ingredients.

In some cases, a dietary supplement composition provided herein can include *ginseng* extract that includes one or more ginsenosides. In some cases, a dietary supplement composition provided herein can include *ginseng* extract that includes between 1% and 20% ginsenosides (e.g., between 3% and 15% ginsenosides, or between 5% and 10% ginsenosides). For example, Korean red *ginseng* extract can include about 7 percent ginsenosides. In some cases, a dietary supplement composition provided herein can include *ginseng* extract that includes ginsenoside Rg1 and/or ginsenoside Rg3. In some cases, a dietary supplement composition provided herein can include Ginsenoside Rg3 in an amount effective to increase glucose uptake both in the basal and insulin-induced states of L6 myotubes, to improve insulin signaling and glucose uptake, or to suppress the progression of type 2 diabetes by inhibiting FFA-mediated loss of beta-cells.

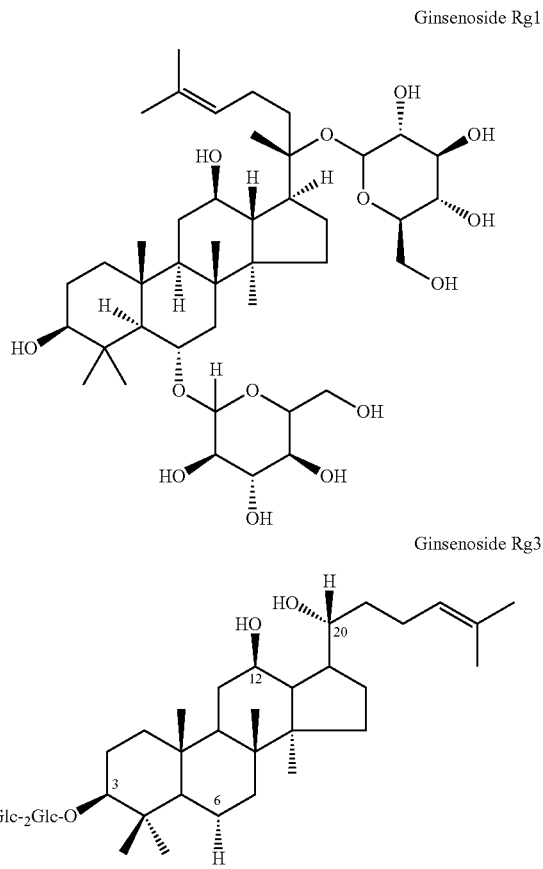

Any appropriate amount of sweet potato extract(s) can be included within a dietary supplement composition provided herein. For example, a dietary supplement composition provided herein can include up to up to 1000 mg of *ginseng* extract per serving (e.g., up to 800 mg/serving, up to 600 mg/serving, up to 400 mg/serving, up to 300 mg/serving, up to 250 mg/serving, or up to 225 mg/serving). In some cases, a dietary supplement composition provided herein can include at least 10 mg of *ginseng* extract per serving (e.g., at least 50 mg/serving, at least 100 mg/serving, at least 150 mg/serving, or at least 175 mg/serving). In some cases, a dietary supplement composition provided herein can include between 10 and 1000 mg of *ginseng* extract per serving, between 50 and 600 mg of *ginseng* extract per serving, between 100 and 300 mg of *ginseng* extract per serving, or between 175 and 225 mg of *ginseng* extract per serving.

In some cases, a dietary supplement composition provided herein can be in the form of a beverage and the amounts per serving of *ginseng* extract(s) described herein can be per 8 fluid ounce serving of that beverage. In some cases, a dietary supplement composition provided herein can be in a powdered form adapted to be mixed with a liquid to form a beverage and the amounts per serving of *ginseng* extract(s) described herein can be per 30 grams of the powdered dietary supplement composition. In some cases, a dietary supplement composition provided herein can be part of an encapsulated dietary supplement having the amounts per serving of *ginseng* extract(s) described herein.

In some cases, a dietary supplement composition provided herein can be in a powdered form and include between 0.1 weight percent and 5.0 weight percent *ginseng* extract(s) (e.g., between 0.3 weight percent and 3.0 weight percent, between 0.5 weigh percent and 1.5 weight percent, between 0.6 weigh percent and 1.0 weight percent, or between 0.8 weight percent and 0.9 weight percent).

A dietary supplement composition provided herein can include one or more additional ingredients. For example, a dietary supplement composition provided herein can include protein, carbohydrates, soluble fiber, flavorants, artificial sweeteners, preservatives, fillers, thickeners, colorants, and any other food safe additive. In some cases, a dietary supplement composition provided herein can include one or more fillers or thickeners selected from the following: a hydroxyl containing compound, a dextrin or dextrin derivative, carboxymethyl cellulose, hydroxypropyl cellulose, hydroxyethyl cellulose, hydroxypropyl methyl cellulose, methyl cellulose, calcium caseinate, konjac, collagen, inulin, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, *psyllium* seed, chitin, chitosan, gum acacia, polyvinyl pyrrolidone, polyethylene oxide, polyvinyl alcohol, or a combination thereof. In some cases, a dietary supplement composition provided herein can include between 0 and 5 weight percent thickener(s). In some cases, a dietary supplement composition provided herein can be substantially free of artificial colors, artificial flavors, and chemical preservatives.

A dietary supplement composition provided herein can include one or more proteins. In some cases, a dietary supplement composition provided herein can include between 5 and 25 grams of protein (e.g., about 10 grams of protein) per 8 fluid ounces of a dietary supplement beverage or for 30 grams of a powdered dietary supplement composition provided herein. In some cases, a dietary supplement composition provided herein can be in a powdered form and include between 5 weight percent and 85 weight percent protein(s) (e.g., between 10 weight percent and 50 weight percent, between 15 weigh percent and 35 weight percent, between 30 weigh percent and 60 weight percent, or between 10 weight percent and 20 weight percent). For example, a dietary supplement composition provided herein can include between 10 weight percent and 13 weight percent of soy protein, between 8 weight percent and 10 weight percent whey protein concentrate, and/or between 5 weight percent and 7 weight percent whey protein isolate. Examples of proteins that can be included in a dietary supplement composition provided herein include dairy protein, soy protein, whey protein, or a combination thereof.

In some cases, a dietary supplement composition provided herein can include less than 10 grams of total fat. In some cases, a dietary supplement composition provided herein can be substantially free of hydrogenated or trans fats.

In some cases, a dietary supplement composition provided herein can include less than 5 grams of sugars (e.g., less than 2 grams of sugars) per 8 fluid ounces of a dietary supplement beverage or for 30 grams of a powdered dietary supplement composition provided herein. In some cases, a dietary supplement composition provided herein can be in a powdered form and include less than 20 weight percent sugar(s) (e.g., less than 15 weight percent, less than 10 weight percent, or less than 5 weight percent). For example, a dietary supplement composition provided herein can be free of added sugars. In some cases, a dietary supplement composition provided herein can be substantially free of corn syrup. In some cases, a dietary supplement composition provided herein can include high intensity sweeteners such as *stevia*, saccharin, aspartame, sucralose, or acesulfame potassium. In some cases, a dietary supplement composition provided herein can include less than 5 weight percent high intensity sweetener(s) (e.g., less than 1 weight percent high intensity sweetener(s)).

In some cases, a dietary supplement composition provided herein can include less than 10 grams of soluble fiber (e.g., less than 6 grams of soluble fiber) per 8 fluid ounces of a dietary supplement beverage or for 30 grams of a powdered dietary supplement composition provided herein. In some cases, soluble fiber in the dietary supplement compositions provided herein can include maltodestrin fiber. In some cases, a dietary supplement composition provided herein can be in a powdered form and include less than 35 weight percent soluble fiber (e.g., less than 25 weight percent, less than 20 weight percent, less than 10 weight percent, between 5 weight percent and 35 weight percent soluble fiber, or between 15 weight percent and 25 weight percent soluble fiber).

In some cases, a dietary supplement composition provided herein can be substantially free of vitamins or mineral fortification other than chromium. In some cases, a dietary supplement composition provided herein can include non-chromium vitamins or mineral fortifications.

A dietary supplement composition provided herein can have a variety of flavorants. For example, a dietary supplement composition provided herein can include vanilla extract, cocoa powder, artificial vanilla flavorant, artificial chocolate flavorant, cream, dried cream extracts, or a combination thereof. In some cases, a dietary supplement composition can have a vanilla, chocolate or vanilla caramel flavor profile. In some cases, a dietary supplement composition provided herein can include salt.

A method for controlling blood glucose concentrations can include consuming a dietary supplement composition provided herein. In some cases, a method for controlling blood glucose concentrations provided herein can include consuming a dietary supplement composition provided herein with a meal. For example, a dietary supplement composition provided herein can be consumed within 10 minutes of consuming a meal (e.g., within 5 minutes of consuming a meal or between bites of a meal). In some cases, a method for controlling blood glucose concentrations provided herein can include consuming a dietary supplement composition provided herein between meals. In some cases, a method for controlling blood glucose concentrations provided herein can include mixing a powdered dietary supplement composition with a liquid to make a beverage. For example, the powdered dietary supplement composition can be provided in a single serving package or in a bulk package.

A dietary supplement composition provided herein can increase the ability of insulin-sensitized cells to uptake glucose, reduce fasting blood glucose levels, lower the glycemic index of foods consumed therewith, reduce insulin resistance, improve glucose tolerance, up-regulate Glucokinase MRNA expression, activate insulin receptors, increase glycogen synthase activity, and/or stimulate the release of insulin. In some cases, a dietary supplement composition provided herein can aid in insulin uptake/release, and support normal metabolism of blood sugar.

EXAMPLES

Example 1—Dietary Supplement Composition

A dietary supplement composition is produced to have the active ingredients shown in Table 1 as well as about 10 grams/serving of dairy and/or soy protein, less than 5 grams/serving of fat (with no hydrogenated or trans fats), less than 2 grams/serving of sugars (with no added sugars), and less than 6 grams/serving of soluble fibers. The serving size can be about 30 grams of dry powder or 8 fluid ounces.

TABLE 1

| Active Ingredients | Amount per serving |
|---|---|
| Chromium | 120 µg/serving |
| Mulberry Extract (>1% DNJ) | 600 mg/serving |
| Sweet Potato Extract | 200 mg/serving |
| Green Tea Extract (>85% phenols) | 120 mg/serving |
| Cinnamon Extract (30% phenols) | 200 mg/serving |
| Korean Red Ginseng extract (7% ginsenosides) | 250 mg/serving |

Example 2—Dietary Supplement Composition

A dietary supplement composition is produced to have the ingredients shown in Table 2.

TABLE 2

| INGREDIENTS | PERCENT % w/w |
|---|---|
| Oil Creamer (Non-Dairy) | 18 to 22 |
| Soy Protein | 10 to 13 |
| Whey Protein Concentrate | 8 to 10 |
| Whey Protein Isolate | 5 to 7 |
| Calcium Caseinate | 5 to 7 |
| Maltodextrin Fiber | 15 to 25 |
| Inulin | 0 to 5 |
| Thickener | 0 to 5 |
| High Intensity Sweetener | 0 to 1 |
| Salt | 0 to 1 |
| Flavorants | 0 to 25 |
| Chromium Oligofructose Complex | 0.03 to 0.05 |
| Mulberry Extract | 1 to 3 |
| Ginseng Extract | 0.3 to 2 |
| Cinnamon Bark Extract | 0.2 to 2 |
| Sweet Potato Powder | 0.2 to 2 |
| Green Tea Extract | 0.1 to 1 |

Example 3—Dietary Supplement Composition

A dietary supplement composition is produced to have the ingredients shown in Table 3.

TABLE 3

| INGREDIENTS | PERCENT % w/w |
|---|---|
| Oil Creamer (Non-Dairy) | 20 to 25 |
| Soy Protein | 10 to 13 |
| Whey Protein Concentrate | 8 to 12 |
| Whey Protein Isolate | 5 to 8 |
| Calcium Caseinate | 5 to 7 |
| Maltodextrin Fiber | 15 to 25 |
| Inulin | 5 to 15 |
| Thickener | 0 to 5 |
| High Intensity Sweetener | 0 to 1 |
| Salt | 0 to 2 |
| Flavorants | 0 to 5 |
| Chromium Oligofructose Complex | 0.03 to 0.05 |
| Mulberry Extract | 1 to 3 |
| Ginseng | 0.3 to 2 |
| Cinnamon Bark Extract | 0.2 to 2 |
| Sweet Potato Powder | 0.2 to 2 |
| Green Tea | 0.1 to 1 |

Example 4—Testing of Dietary Supplement Compositions

A sample population of prediabetic participants, sufficient to establish a statistically valid confidence interval, took part in a 56-day study. After protocol approval by the Institutional Review Board, male and female subjects between 18-45 years of age were prescreened to meet the inclusion and exclusion criteria. Subjects with an A1C range of 5.5%-6.4% were eligible for the study. A1C levels of 5.6% or below are considered normal. A1C levels of 6.5% or greater are indicative of diabetes. A1C levels greater than 5.6% but less than 6.5% are in the range of prediabetes.

For each participant the study concluded after 56 days from enrollment and included four (4) follow-ups. Informed consent from each participant was obtained before being administrated dietary supplement compositions having the ingredients listed in Table 3.

On Day 0 (baseline), medical history and physical examinations were performed on all participants. Blood collections were performed at time points 0 (baseline), 90, and 150 minutes on Day 0. All participants fasted prior to testing. Each participant consumed the dietary supplement compositions having the ingredients listed in Table 3 immediately after time point 0 (baseline) and before time point 30 minutes. All study participants continued a 56-day treatment. Subsequent blood chemistries were performed on all participants on Days 28, 42 and 56 at time point 0 minutes, to be tested for the selected biomarkers.

Scored questionnaires, consisting of a psychometric response scale, were used to measure subjective data on Day 0 (baseline). All participants completed subsequent scored questionnaires on days 28, 42, and 56 to assess subjective levels of energy and satiety. The participants were given dietary supplement compositions similar to those provided in Examples 2 and 3 and told to take the product twice a day.

Unpaired t Test Results:

The tested dietary supplement compositions showed the following results, shown in Table 4, when comparing baseline (Day 0) to end point (Day 56). There was a statistically significant reduction (p=0.00003) in A1C levels. There was a statistically significant reduction (p=0.00005) in serum glucose levels. There was a statistically significant reduction (p=0.0067) in insulin levels. There was a reduction in HOMA levels, but the reduction was not statistically significant (p=0.3540).

TABLE 4

| Variable | Baseline (MEAN ± SE) | Day 56 (MEAN ± SE) | Improvement (%) | Normal Ranges |
|---|---|---|---|---|
| HbA1C | 5.859 ± 0.054 | 5.566 ± 0.054 | 5 | 4.6-5.4 mg/dl |
| Glucose | 102.6 ± 1.63 | 94.24 ± 1.55 | 8.14 | 70-100 mg/dL |
| Insulin | 53.7 ± 2.48 | 45.06 ± 1.80 | 16.08 | 2 6-24.9 µg/mL |
| HOMA | 4.18 ± 0.40 | 3.67 ± 0.36 | 12.16 | 1-4 |

Figure 1:
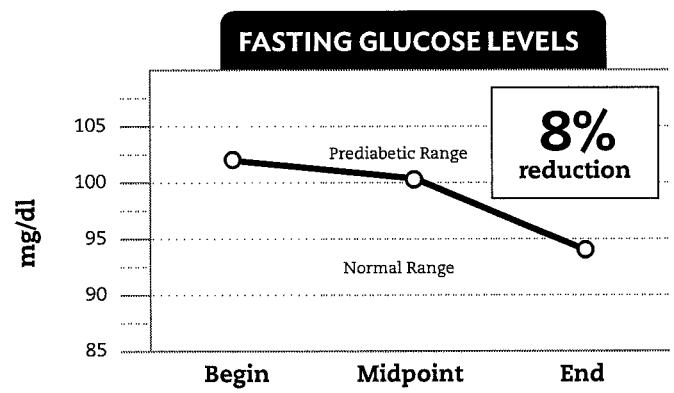
FIG. 1 is a chart of the fasting glucose levels of test participants using a dietary supplement composition provided herein.

FIG. 1 depicts the fasting glucose levels for the test subjects consuming the tested dietary supplement compositions over the course of the study (56 days). As shown, the test subjects reported an 8% decrease in fasting glucose levels over the course of the study.

Figure 3:
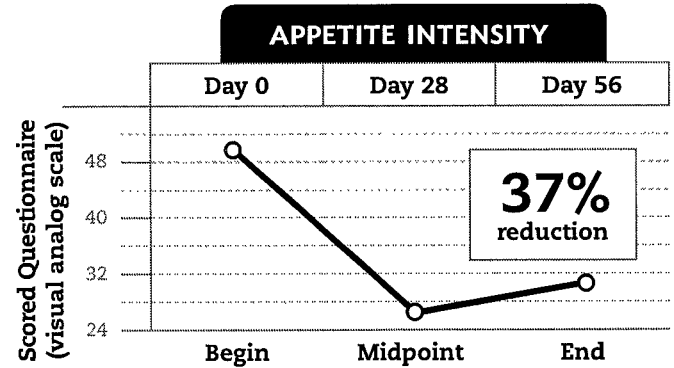
FIG. 3 is a chart of appetite intensity levels of test participants using a dietary supplement composition provided herein.

Scored Questionnaire Results:

Each test subject was asked to complete a questionnaire on Days 0, 28, and 56. In order to measure energy levels and satiety, each test subject was asked to rate his/her intensity of energy, intensity of fatigue, current degree of hunger, and current assessment of how much they could eat along a 100 mm horizontal line. The subjects completed the questionnaire by placing a vertical slash on the line corresponding to their sensation for each question. FIG. 2 shows how the fatigue intensity changed over the course of the study. As shown, test subjects using the tested dietary supplement compositions reported a 54% decrease in fatigue over the course of the study. FIG. 3 shows how the appetite intensity changed over the course of the study. As shown, test subjects using the tested dietary supplement compositions reported a 37% decrease in appetite intensity over the course of the study.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A powdered dietary supplement composition contained in a bulk package, the bulk package containing a measuring scoop and the powdered dietary supplement composition, the measuring scoop being sized to scoop an amount of the powdered dietary supplement composition suitable for blending with a liquid to form a beverage, wherein the amount of the powdered dietary supplement composition is 15 to 60 g and consists essentially of:
  a) between 10 and 50 weight percent protein, wherein the protein comprises dairy protein, soy protein, whey protein, or a combination thereof;
  b) between 5 weight percent and 35 weight percent maltodextrin fiber;
  c) between 18 weight percent and 25 weight percent oil creamer;
  d) between 10 mg and 1000 mg sweet potato extract;
  e) between 20 µg and 360 µg chromium; and
  f) an extract or extracts selected from the group consisting of:
    i) between 50 mg and 5000 mg mulberry extract;
    ii) between 10 mg and 1000 mg green tea extract;
    iii) between 10 mg and 1000 mg cinnamon extract;
    iv) between 10 mg and 1000 mg *ginseng* extract; and
    v) combinations thereof;
and wherein the dietary supplement composition optionally comprises
  g) one or more of an artificial sweetener, a flavorant, inulin, calcium caseinate, salt, and a component selected from the group consisting of dextrin, carboxymethyl cellulose, hydroxypropyl cellulose, hydroxyethyl cellulose, hydroxypropyl methyl cellulose, methyl cellulose, konjac, collagen, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, *psyllium* seed, chitin, chitosan, gum acacia, polyvinyl pyrrolidone, polyethylene oxide, and polyvinyl alcohol.

2. The powdered dietary supplement composition of claim 1, wherein:
  i. said mulberry extract present in an amount between 50 mg and 5000 mg per serving;
  ii. said green tea extract is present in an amount between 10 mg and 1000 mg per serving;
  iii. said cinnamon extract is present in an amount between 10 mg and 1000 mg per serving; and
  iv. said *ginseng* extract is present in an amount between 10 mg and 1000 mg per serving.

3. The powdered dietary supplement composition of claim 1, wherein said protein is present in an amount of between 10 and 13 weight percent soy protein per serving, between 8 and 10 weight percent whey protein concentrate per serving, and between 5 and 7 weight percent whey protein isolate per serving.

4. The powdered dietary supplement composition of claim 1, wherein said maltodextrin fiber is present in an amount between 15 and 25 weight percent per serving.

5. The powdered dietary supplement composition of claim 1, wherein said oil creamer is present in an amount between 20 to 25 weight percent per serving.

6. The powdered dietary supplement composition of claim 1, wherein said sweet potato extract is present in an amount between 50 mg and 600 mg per serving.

7. The powdered dietary supplement composition of claim 1, wherein said chromium is present in an amount between 50 µg and 180 µg per serving.

8. The powdered dietary supplement composition of claim 1, wherein said mulberry extract is present in an amount between 50 mg and 5000 mg per serving.

9. The powdered dietary supplement composition of claim 1, wherein said green tea extract is present in an amount between 10 mg and 1000 mg per serving.

10. The powdered dietary supplement composition of claim 1, wherein said cinnamon extract is present in an amount between 10 mg and 1000 mg per serving.

11. The powdered dietary supplement composition of claim 1, wherein said *ginseng* extract is present in an amount between 10 mg and 1000 mg per serving.

12. The powdered dietary supplement composition of claim 1, wherein said amount is adapted to produce an 8 fluid ounce serving of the beverage.

13. The powdered dietary supplement composition of claim 1, wherein the powdered dietary supplement composition contains:
  chromium in the form of chromium oligofructose complex, wherein the composition contains 1 to 20 mg chromium oligofructose complex;
  400 to 800 mg mulberry extract;
  100 to 300 mg sweet potato extract;
  50 to 200 mg green tea extract;
  100 to 300 mg cinnamon extract; and
  100 to 400 mg *ginseng* extract.

14. The powdered dietary supplement composition of claim 1, wherein said composition contains 5 to 25 grams of protein per serving.

15. The powdered dietary supplement composition of claim 1, wherein said amount contains less than 10 grams of total fat per serving.

16. The powdered dietary supplement composition of claim 1, wherein said amount contains less than 5 grams of sugars per serving.

17. The powdered dietary supplement composition of claim 1, wherein the powdered dietary supplement composition contains less than 10 grams of soluble fiber per serving.

18. The powdered dietary supplement composition of claim 1, wherein the green tea extract contains less than 85% phenols.

19. The powdered dietary supplement composition of claim 1, wherein the cinnamon extract contains between 20% and 40% phenols.

20. The powdered dietary supplement composition of claim 1, wherein the *ginseng* extract contains less than 20% ginsenosides, or between 5% and 10% ginsenosides.

21. The powdered dietary supplement composition of claim 1, wherein the *ginseng* extract is Korean Red *ginseng* extract.

22. The powdered dietary supplement composition of claim 1, wherein the powdered dietary supplement composition is substantially free of hydrogenated or trans fats.

23. The powdered dietary supplement composition of claim 1, wherein said artificial sweetener is present in said composition, and wherein said artificial sweetener is selected from the group consisting of saccharine, sucralose, aspartame, acesulfame potassium, and combinations thereof.

24. The powdered dietary supplement composition of claim 1, wherein said flavorant is present in said composition, and wherein said flavorant is selected from the group consisting of vanilla extract, cocoa powder, artificial vanilla flavorant, artificial chocolate flavorant, cream, dried cream extracts, caramel, and combinations thereof.

25. The powdered dietary supplement composition of claim 1, wherein said component selected from the group consisting of dextrin, carboxymethyl cellulose, hydroxypropyl cellulose, hydroxyethyl cellulose, hydroxypropyl methyl cellulose, methyl cellulose, konjac, collagen, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, *psyllium* seed, chitin, chitosan, gum acacia, polyvinyl pyrrolidone, polyethylene oxide, polyvinyl alcohol, and combinations thereof is present in said composition.

26. The powdered dietary supplement composition of claim 1, wherein said inulin is present in said composition, and wherein the inulin makes up no more than 15 weight percent of the powdered dietary supplement composition.

27. The powdered dietary supplement composition of claim 26, wherein the inulin makes up between 5 and 15 weight percent of the powdered dietary supplement composition, or between 0 and 5 weight percent of the powdered dietary supplement composition.

28. The powdered dietary supplement composition of claim 1, wherein said calcium caseinate is present in said composition, and wherein the calcium caseinate makes up between 5 and 7 weight percent of the powdered dietary supplement composition.

29. The powdered dietary supplement composition of claim 1, wherein said salt is present in said composition, and wherein the salt makes up up to 2 weight percent of the powdered dietary supplement composition.

30. The powdered dietary supplement composition of claim 1, wherein said protein contains between 10 and 13 weight percent soy protein, between 8 and 12 percent whey protein concentrate, and between 5 and 8 weight percent whey protein isolate.

31. The powdered dietary supplement composition of claim 1, wherein the powdered dietary supplement composition is substantially free of corn syrup.

32. The powdered dietary supplement composition of claim 1, wherein the powdered dietary supplement composition is substantially free of vitamins or mineral fortification other than the chromium.

33. The powdered dietary supplement composition of claim 1, wherein the amount of the powdered dietary supplement composition is about 30 g.

34. A tablet or capsule consisting essentially of:
between 5 and 85 weight percent of protein, wherein the protein comprises dairy protein, soy protein, whey protein, or a combination thereof;
between 5 weight percent and 35 weight percent maltodextrin fiber;
between 10 mg and 1000 mg sweet potato extract;
between 20 µg and 360 µg chromium; and
an extract or extracts selected from the group consisting of:
i. between 50 mg and 5000 mg mulberry extract;
ii. between 10 mg and 1000 mg green tea extract;
iii. between 10 mg and 1000 mg cinnamon extract;
iv. between 10 mg and 1000 mg *ginseng* extract; and
v. a combination thereof.

35. The tablet or capsule of claim 34, wherein:
a. said mulberry extract is present in an amount between 50 mg and 5000 mg;
b. said green tea extract is present in an amount between 10 mg and 1000 mg;
c. said cinnamon extract is present in an amount between 10 mg and 1000 mg; and
d. said *ginseng* extract is present in an amount between 10 mg and 1000 mg.

36. The tablet or capsule of claim 34, wherein said tablet or capsule contains the mulberry extract in an amount of between 50 mg and 5000 mg.

37. The tablet or capsule of claim 34, wherein said tablet or capsule contains the green tea extract in an amount of between 10 mg and 1000 mg.

38. The tablet or capsule of claim 34, wherein said tablet or capsule contains the cinnamon extract in an amount of between 10 mg and 1000 mg.

39. The tablet or capsule of claim 34, wherein said tablet or capsule contains the *ginseng* extract in an amount of between 10 mg and 1000 mg.

40. A powdered dietary supplement composition contained in a bulk package, the bulk package containing a measuring scoop and the powdered dietary supplement composition, the measuring scoop being sized to scoop an amount of the powdered dietary supplement composition suitable for blending with a liquid to form a beverage, wherein the amount of the powdered dietary supplement composition consists essentially of:
a) between 10 and 50 weight percent protein, wherein the protein comprises dairy protein, soy protein, whey protein, or a combination thereof;
b) between 5 weight percent and 35 weight percent maltodextrin fiber;
c) between 18 weight percent and 25 weight percent oil creamer;
d) between 0.1 weight percent and 2.0 weight percent sweet potato extract;
e) between 0.01 weight percent and 0.1 weight percent chromium; and
f) an extract or extracts selected from the group consisting of:
i) between 0.5 weight percent and 10 weight percent mulberry extract;
ii) between 0.1 weight percent and 1.0 weight percent green tea extract;

iii) between 0.1 weight percent and 2.0 weight percent cinnamon extract;
iv) between 0.1 weight percent and 5.0 weight percent *ginseng* extract; and
v) combinations thereof;

and wherein the dietary supplement composition optionally comprises g) one or more of an artificial sweetener, a flavorant, inulin, calcium caseinate, salt, and a component selected from the group consisting of dextrin, carboxymethyl cellulose, hydroxypropyl cellulose, hydroxyethyl cellulose, hydroxypropyl methyl cellulose, methyl cellulose, konjac, collagen, casein, wheat gluten, carrageenan, alginates, propylene glycol alginate, xanthan, dextrin, pullulan, curdlan, gellan, locust bean gum, guar gum, tara gum, gum tragacanth, pectin, agar, zein, karaya, gelatin, *psyllium* seed, chitin, chitosan, gum acacia, polyvinyl pyrrolidone, polyethylene oxide, and polyvinyl alcohol.

41. A tablet or capsule consisting essentially of:
between 5 and 85 weight percent of protein, wherein the protein comprises dairy protein, soy protein, whey protein, or a combination thereof;
between 5 weight percent and 35 weight percent maltodextrin fiber;
between 10 mg and 1000 mg sweet potato extract;
between 20 µg and 360 µg chromium; and
an extract or extracts selected from the group consisting of:
  i. between 0.5 weight percent and 10 weight percent mulberry extract;
  ii. between 0.1 weight percent and 1.0 weight percent green tea extract;
  iii. between 0.1 weight percent and 2.0 weight percent extract;
  iv. between 0.1 weight percent and 5.0 weight percent *ginseng* extract; and
  v. a combination thereof.

* * * * *